(12) United States Patent
Edwards (10) Patent No.: US 11,918,246 B2
(45) Date of Patent: Mar. 5, 2024

(54) MEDICAL DEVICE INCLUDING FLEXIBLE SHAFT WITH MULTIPLE BEARINGS

(71) Applicant: GYRUS ACMI, INC., Southborough, MA (US)

(72) Inventor: Kevin Cooper Edwards, Olive Branch, MS (US)

(73) Assignee: Gyrus ACMI, Inc., Westborough, MA (US)

(*) Notice: Subject to any disclaimer, the term of this patent is extended or adjusted under 35 U.S.C. 154(b) by 371 days.

(21) Appl. No.: 17/168,985

(22) Filed: Feb. 5, 2021

(65) Prior Publication Data
US 2021/0244433 A1     Aug. 12, 2021

Related U.S. Application Data (60) Provisional application No. 62/971,556, filed on Feb. 7, 2020.

(51) Int. Cl.
*A61B 17/3207* (2006.01)

(52) U.S. Cl.
CPC .................. *A61B 17/3207* (2013.01)

(58) Field of Classification Search
CPC ........ A61B 17/3207; A61B 17/320758; A61B 17/320783; A61B 17/32002; A61B 2017/320766; A61B 2017/320028; A61B 2017/320032; A61M 39/08
See application file for complete search history.

(56) References Cited

U.S. PATENT DOCUMENTS

| | | | | |
|---|---|---|---|---|
| 4,662,404 A | * | 5/1987 | LeVeen | A61M 39/08 138/155 |
| 8,382,783 B2 | | 2/2013 | Suzuki | |
| 8,393,242 B2 | * | 3/2013 | Ozaki | B23B 39/14 901/41 |

(Continued)

FOREIGN PATENT DOCUMENTS

| | | |
|---|---|---|
| DE | 102012101259 A1 | 8/2013 |
| EP | 1598023 A2 | 11/2005 |

(Continued)

OTHER PUBLICATIONS

"European Application Serial No. 21155616.2, Extended European Search Report dated Jul. 2, 2021", 8 pgs.

*Primary Examiner* — Wade Miles
(74) *Attorney, Agent, or Firm* — Schwegman Lundberg Woessner, P.A.

(57) ABSTRACT

A surgical device, such as a debrider, can include an elongated inner shaft that is movable within an elongated, hollow outer shaft. An actuator can controllably impart movement to a proximal portion of the inner shaft. A cutting element, located at a distal portion of the inner shaft, can move with the inner shaft. The outer shaft can expose the cutting element as the inner shaft moves. The inner shaft can include a flexible inner shaft portion. A plurality of bearings, located between the inner shaft and the outer shaft along the flexible inner shaft portion, can space the flexible inner shaft portion with respect to the outer shaft as the inner shaft moves. The plurality of bearings can help reduce friction between the inner shaft and the outer shaft and help maintain concentricity of the inner shaft and the outer shaft.

20 Claims, 6 Drawing Sheets

(56) References Cited

U.S. PATENT DOCUMENTS

| | | | | |
|---|---|---|---|---|
| 2002/0007190 | A1* | 1/2002 | Wulfman | A61B 17/320758 |
| | | | | 606/171 |
| 2014/0373840 | A1* | 12/2014 | Graham | A61M 16/1095 |
| | | | | 128/203.12 |
| 2015/0230821 | A1* | 8/2015 | Batchelor | A61B 17/320758 |
| | | | | 606/180 |
| 2016/0235469 | A1* | 8/2016 | Prisco | A61B 18/1485 |
| 2018/0368873 | A1 | 12/2018 | Edwards et al. | |
| 2020/0384187 | A1* | 12/2020 | Pham | A61M 25/0054 |

FOREIGN PATENT DOCUMENTS

| | | | |
|---|---|---|---|
| EP | 2436320 A1 | 4/2012 | |
| WO | WO-2014123874 A1 | 8/2014 | |

\* cited by examiner

MEDICAL DEVICE INCLUDING FLEXIBLE SHAFT WITH MULTIPLE BEARINGS

CROSS-REFERENCE TO RELATED APPLICATION

This application claims the benefit of U.S. Provisional Application No. 62/971,556, filed Feb. 7, 2020, which is hereby incorporated by reference in its entirety.

FIELD OF THE DISCLOSURE

The present disclosure relates generally to a medical device, such as a debrider.

BACKGROUND OF THE DISCLOSURE

A medical device, such as a debrider, can remove tissue, such as in a medical procedure referred to as debridement.

SUMMARY

This document describes, among other things, a surgical device, such as a debrider. An elongated inner shaft can move within an elongated, hollow outer shaft. A plurality of bearings, located between the inner shaft and the outer shaft along a flexible portion of the inner shaft, can space the flexible portion with respect to the outer shaft as the inner shaft moves. The plurality of bearings can help reduce friction between the inner shaft and the outer shaft and help maintain concentricity of the inner shaft and the outer shaft.

In an example, a surgical device can include: an elongated, hollow outer shaft; an elongated inner shaft movable within the outer shaft and including a flexible inner shaft portion that is more flexible than at least one of a more proximal or more distal portion of the inner shaft; a cutting element located at a distal portion of the inner shaft and configured to move with the inner shaft, the outer shaft configured to expose the cutting element as the inner shaft moves; and a plurality of bearings located between the inner shaft and the outer shaft along a length of the inner shaft, the bearings configured to space the flexible inner shaft portion with respect to the outer shaft as the inner shaft moves.

In an example, a method for operating a surgical device can include: providing an elongated, hollow outer shaft; actuating a proximal portion of an elongated inner shaft that is at least partially disposed within the outer shaft to impart movement to the inner shaft, the inner shaft including a flexible inner shaft portion that is more flexible than at least one of a more proximal or more distal portion of the inner shaft; moving, via the inner shaft, a cutting element located at a distal portion of the inner shaft, the outer shaft configured to expose the cutting element as the inner shaft moves; and positioning, via a plurality of bearings located between the inner shaft and the outer shaft along a length of the inner shaft, the flexible inner shaft portion to be substantially coaxial with the outer shaft as the inner shaft moves.

In an example, a surgical device can include: an elongated, hollow outer shaft; an elongated inner shaft movable within the outer shaft and including a flexible inner shaft portion that is more flexible than at least one of a more proximal or more distal portion of the inner shaft; an actuator configured to controllably impart movement to a proximal portion of the inner shaft, the inner shaft being configured to transmit the imparted movement along the inner shaft to a distal portion of the inner shaft, the imparted movement being at least one of single-direction rotation about a central axis, oscillating rotation about the central axis, or reciprocating translation along the central axis; a cutting element located at the distal portion of the inner shaft and configured to move with the inner shaft, the outer shaft configured to expose the cutting element as the inner shaft moves; and a plurality of bearings located between the inner shaft and the outer shaft along the flexible inner shaft portion, the bearings configured to space the flexible inner shaft portion with respect to the outer shaft as the inner shaft moves.

BRIEF DESCRIPTION OF THE DRAWINGS

Corresponding reference characters indicate corresponding parts throughout the several views. Elements in the drawings are not necessarily drawn to scale. The configurations shown in the drawings are merely examples and should not be construed as limiting in any manner.

DETAILED DESCRIPTION

This document describes, among other things, a surgical device, such as a debrider. An elongated inner shaft can move within an elongated, hollow outer shaft. A plurality of bearings, located between the inner shaft and the outer shaft along a flexible portion of the inner shaft, can space the flexible portion with respect to the outer shaft as the inner shaft moves. The plurality of bearings can help reduce friction between the inner shaft and the outer shaft and help maintain concentricity of the inner shaft and the outer shaft.

In surgical debridement, a practitioner can use a debrider to remove dead, damaged, or infected tissue (e.g., soft tissue and/or bone). Using a debrider to remove the tissue can be quicker and can provide more control than cutting away the tissue with a scalpel.

In a debrider, an elongated, hollow outer shaft can include a flexible outer shaft portion. An elongated inner shaft can move (e.g., rotate and/or reciprocatingly translate) within the outer shaft. The inner shaft can include a flexible inner shaft portion that is disposed within the flexible outer shaft portion and can flex with the flexible outer shaft portion. A cutting element, disposed on a distal portion of the inner shaft, can move with the inner shaft. The outer shaft can expose the cutting element as the inner shaft moves. A plurality of bearings can be disposed between the inner shaft and the outer shaft along a length of the inner shaft. The length can include at least some of the flexible inner shaft portion. The bearings can position the flexible inner shaft portion to be substantially coaxial with the flexible outer shaft portion as the inner shaft moves.

Compared to debriders that use only a single bearing, such as at a proximal region of a flexible portion or a distal region of a flexible portion, the debrider described herein can have reduced friction between the inner and outer shafts, which can ease a load on an actuator that drives the inner shaft, can reduce wear on the inner and outer shafts, and can reduce noise and vibration from the debrider during use.

Figure 1:
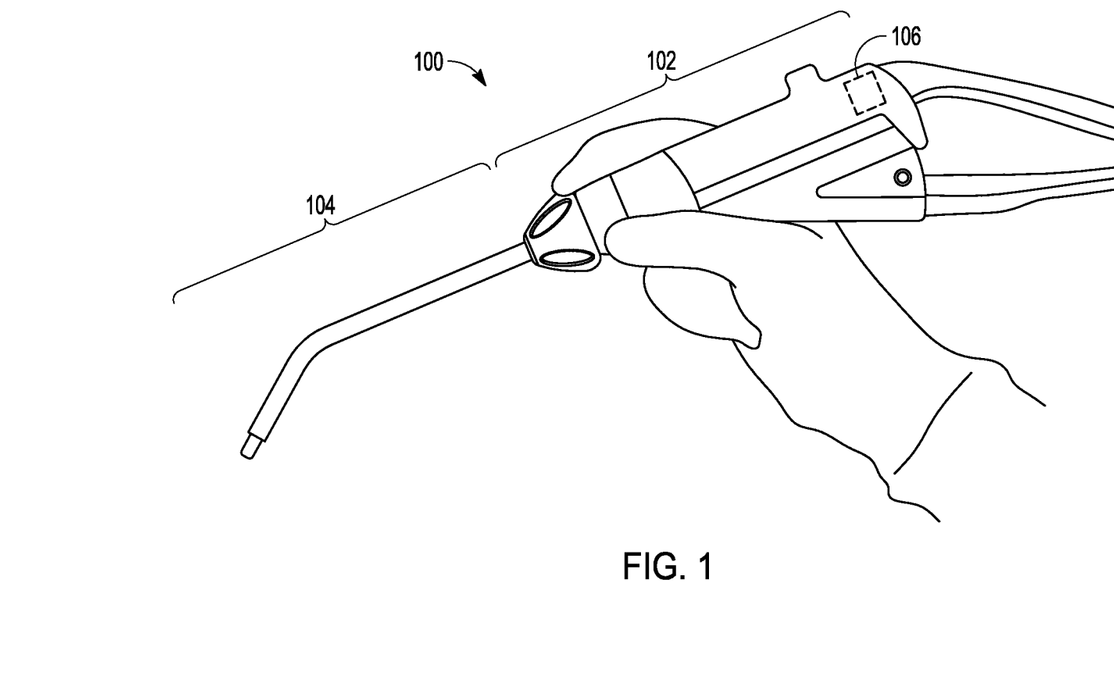
FIG. 1 shows an example of a debrider.

FIG. 1 shows an example of a debrider 100. In the example of FIG. 1, the debrider 100 can be shaped and sized to be handheld by a practitioner during use (e.g., a microdebrider). The features of the debrider 100, explained in detail below, can also be used on debriders that need not be handheld by a practitioner during use. For example, the debrider 100 can be controlled robotically, rather than handheld. Many of the features and components of the debrider 100 can be scaled up or down as needed, depending on the particular application of the debrider 100.

The debrider 100 can include a proximal portion 102. The proximal portion 102 can include a handle, which can be shaped to be gripped by a practitioner during use. The proximal portion 102 can include controls, such as a power button, and connections to electrical power, suction, and the like. The proximal portion 102 can include a motor and/or actuator 106, which can impart motion to an inner shaft within a distal portion 104 of the debrider 100.

The debrider 100 can include a distal portion 104 extending distally from the proximal portion 102. The distal portion 104 can include an outer shaft that remains stationary with respect to the proximal portion 102 during use. The distal portion 104 can include an inner shaft that rotates and/or reciprocatingly translates within the outer shaft, in response to motion imparted by the actuator 106 in the proximal portion 102. The distal portion 104 can include a cutting element, such as a blade or a burr, that is positioned at a distal end of the inner shaft. The outer shaft can expose the cutting element as the cutting element moves with the inner shaft. For example, for configurations in which the cutting element is a blade or a burr, the outer shaft can include an aperture at or near a distal end of the outer shaft. The aperture can extend only partially around a circumference or outer perimeter of the outer shaft, to confine the cutting area to a relatively small area. As another example, for configurations in which the cutting element is a burr, the outer shaft can expose the burr around a full circumference or outer perimeter of the outer shaft. Other configurations can also be used.

Many of the features described herein are directed toward the construction and placement of bearings that allow the inner shaft to rotate and/or reciprocatingly translate within the outer shaft. Because the bearing construction and placement may not depend on the nature of the proximal portion 102, the drawings and discussion that follow focus largely on the distal portion 104. The features described herein can be used with any suitable proximal portion 102 of the debrider 100.

Figure 2:
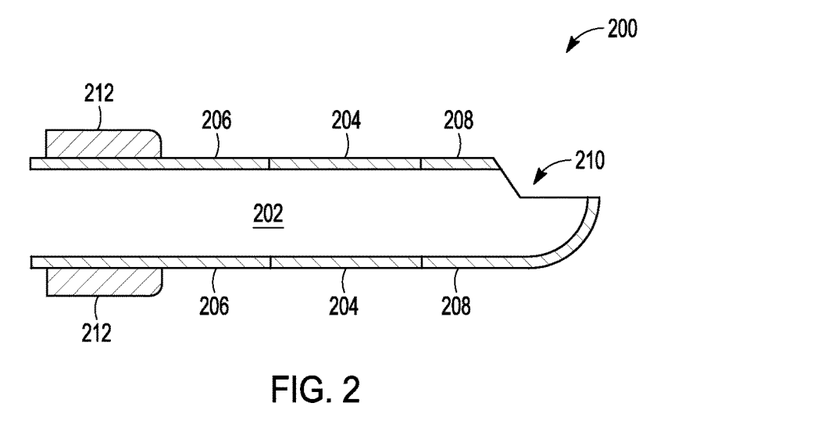
FIG. 2 shows a cross-sectional view of an example of an outer shaft.

FIG. 2 shows a cross-sectional view of an example of an outer shaft 200. The outer shaft 200 can be used in the distal portion 104 of the debrider 100, or in any suitable debrider. The outer shaft 200 is but one example of an outer shaft 200; other configurations can also be used.

The outer shaft 200 can be elongated and hollow. During use, the outer shaft 200 can remain relatively stationary, with respect to the proximal portion 102. This, the practitioner can hold the outer shaft 200 during use. The practitioner can allow a surface of the outer shaft 200 to incidentally contact tissue without damaging the tissue. The moving elements in the debrider 100 can be located within the elongated, hollow interior 202 of the outer shaft 200, such as explained below, and can debride the tissue through an aperture on the outer shaft 200.

The outer shaft 200 can include one or more rigid portions. Each rigid portion can retain its shape in response to a deforming force applied by a practitioner and/or applied by a manufacturer of the debrider 100. The outer shaft 200 can include one or more bends that are rigid. A practitioner can use the one or more bends to help access a particular region of tissue on a patient.

The outer shaft 200 can include one or more bendable or semi-rigid portions. A practitioner can apply a deforming force to a bendable or semi-rigid portion, to bend the bendable or semi-rigid portion into a desired shape, such as to form or modify a bend. After such a deformation, the bendable or semi-rigid portion can retain its shape, such as to be used in a later step of a procedure. For example, a practitioner can bend a bendable or semi-rigid portion of the outer shaft 200 to form a 90-degree bend in the outer shaft 200, then can use the 90-degree bend in the outer shaft 200 to help access a particular region of tissue on a patient. A bendable or semi-rigid portion of the outer shaft 200 can be more flexible than a rigid portion of the outer shaft 200.

The outer shaft 200 can include one or more pliable portions. Each pliable portion can deform under its own weight, such that the pliable portion may not retain a specific shape. A practitioner can use the one or more pliable portions to deform the outer shaft 200 as needed during a procedure to access a particular region of tissue on a patient. A pliable portion of the outer shaft 200 can be more flexible than a bendable or semi-rigid portion of the outer shaft 200.

The outer shaft 200 can vary in its bending flexibility along its length. For example, the outer shaft 200 can optionally include a flexible outer shaft portion 204 that is more flexible than another portion of the outer shaft 200, such as a more proximal portion 206 of the outer shaft 200 or a more distal portion 208 of the outer shaft 200. The flexible outer shaft portion 204 can be bendable or semi-rigid (e.g., capable of being bent into a shape and then retaining the shape). The flexible outer shaft portion 204 can be pliable (e.g., incapable of retaining a shape). The flexible outer shaft portion 204 can be rigid (e.g., more rigid than the more proximal portion 206 of the outer shaft 200 or the more distal portion 208 of the outer shaft 200). The flexible outer shaft portion 204 can be rigid similar to the more proximal portion 206 of the outer shaft 200 or the more distal portion 208 of the outer shaft 200.

The outer shaft 200 can optionally include more than one flexible outer shaft portion 204, which can be separated by one or more portions having less flexibility. The flexible outer shaft portion 204 can be located at a bend in the outer shaft 200. The flexible outer shaft portion 204 can be located adjacent to a bend in the outer shaft 200. The more proximal portion 206 may have a flexibility that is greater than the flexible outer shaft portion 204, equal to the flexible outer shaft portion 204, or less than the flexible outer shaft portion 204. The more distal portion 208 may have a flexibility that is greater than the flexible outer shaft portion 204, equal to the flexible outer shaft portion 204, or less than the flexible outer shaft portion 204. The flexible outer shaft portion 204 can include a different material or materials and/or a different thickness than the portions having less flexibility. For example, the flexible outer shaft portion 204 can be thinner than the portions having less flexibility. In some configurations, a manufacturer of the debrider 100 can remove material from a wall of the outer shaft 200, such as by forming relief cuts in the outer shaft 200, to form the flexible outer shaft portion 204 and bend the outer shaft portion 204 into a desired shape and/or orientation. Other suitable configurations can also be used.

The outer shaft 200 can optionally have a uniform flexibility along its length. The uniformly flexible outer shaft 200 can include one or more pre-formed bends or angles. The bearing configurations described herein can improve performance of devices such as can include one or more bends, such as by reducing a load on the actuator 106 (FIG. 1) that imparts motion to an inner shaft disposed within the outer shaft 200, or reducing friction between the outer shaft 200 and the inner shaft.

The outer shaft 200 can expose the cutting element as the inner shaft moves. For example, the outer shaft 200 can include an aperture 210 at or near a distal end of the outer shaft 200. The aperture 210 can expose the cutting element as the inner shaft moves. During use, the practitioner can position the aperture 210 onto tissue that is to be removed, so that the moving cutting element can shave, scrape, grind, or otherwise excise the tissue through the aperture 210. The debrider 100 can additionally include plumbing such as can supply suction and/or irrigation to the aperture 210, such as via the hollow interior 202 of the outer shaft 200. Optionally, one or more additional small tubes can be affixed along an exterior of the outer shaft 200 to provide suction and/or irrigation.

The outer shaft 200 can include an outer shaft hub 212 such as can anchor the outer shaft 200 against a suitable wall or structure within the proximal portion 102 of the debrider 100.

Figure 3:
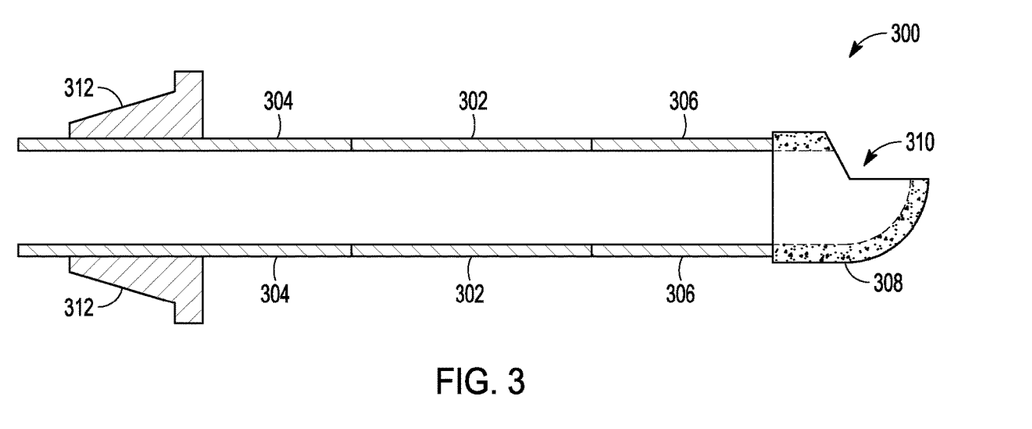
FIG. 3 shows a cross-sectional view of an example of an inner shaft.

FIG. 3 shows a cross-sectional view of an example of an inner shaft 300. The inner shaft 300 can be located and movable within the outer shaft 200 (FIG. 2). The inner shaft 300 can be included in the distal portion 104 of the debrider 100 (FIG. 1) or in any suitable debrider. The inner shaft 300 can be hollow or solid. The inner shaft 300 is but one example of an inner shaft 300; other configurations can also be used.

The inner shaft 300 can be movable within the outer shaft 200. For example, the movement can include at least one of single-direction rotation about a central axis, oscillating rotation about the central axis, or reciprocating translation along the central axis. Other movements can also be used.

The inner shaft 300 can vary in flexibility along its length. For example, the inner shaft 300 can include a flexible inner shaft portion 302 such as can be more flexible than at least one of a more proximal portion 304 or more distal portion 306 of the inner shaft 300. The more proximal portion 304 may have a flexibility that is greater than the flexible inner shaft portion 302, equal to the flexible inner shaft portion 302, or less than the flexible inner shaft portion 302. The more distal portion 306 may have a flexibility that is greater than the flexible inner shaft portion 302, equal to the flexible inner shaft portion 302, or less than the flexible inner shaft portion 302.

At least some of the flexible inner shaft portion 302 can be disposed within the flexible outer shaft portion 204 (FIG. 2). A proximal end of the flexible inner shaft portion 302 and a proximal end of the flexible outer shaft portion 204 can be located at a same longitudinal location along a length of the distal portion 104 of the debrider 100. A proximal end of the flexible inner shaft portion 302 can be located proximal to a proximal end of the flexible outer shaft portion 204 or distal to a proximal end of the flexible outer shaft portion 204. A distal end of the flexible inner shaft portion 302 and a distal end of the flexible outer shaft portion 204 can be located at a same longitudinal location along a length of the distal portion 104 of the debrider 100. A distal end of the flexible inner shaft portion 302 can be located proximal to a distal end of the flexible outer shaft portion 204 or distal to a distal end of the flexible outer shaft portion 204.

A cutting element 308 can be located at a distal portion of the inner shaft 300. The cutting element 308 can move with the inner shaft 300. For example, the movement can include at least one of single-direction rotation about a central axis, oscillating rotation about the central axis, or reciprocating translation along the central axis. Other movements can also be used. The outer shaft 200 can expose the cutting element 308 as the inner shaft 300 moves, such as through the aperture 210. The cutting element 308 can be formed as a shaving blade 310, which can shave a relatively thin layer of tissue for each pass of the shaving blade 310 over the tissue through the aperture 210 in the outer shaft 200.

Figure 4:
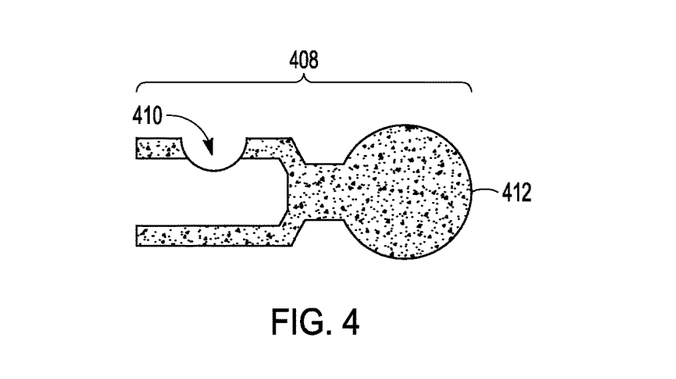
FIG. 4 shows a cross-sectional view of another example of a cutting element.

FIG. 4 shows a cross-sectional view of another example of a cutting element 408. The cutting element 408 can be located at a distal portion of the inner shaft 300 (FIG. 3), in place of the cutting element 308 shown in FIG. 3. The cutting element 408 can include a shaving blade 410, which can shave a relatively thin layer of tissue for each pass of the shaving blade 410 over the tissue through the aperture 210 in the outer shaft 200.

Compared with the cutting element 308 in FIG. 3, the cutting element 408 can additionally include a burr 412 positioned at a distal end of the cutting element 308. The burr 412 can extend beyond a distal end of the outer shaft. During use, a practitioner can use the burr 412 to grind tissue, such as harder tissue and/or bone, as needed. Other cutting elements and mechanisms for removing the tissue can also be used.

The inner shaft 300 can include an inner shaft hub 312 that can rotatably couple the inner shaft 300 to the actuator 106, so that the actuator 106 can impart motion to the inner shaft 300.

Figure 5:
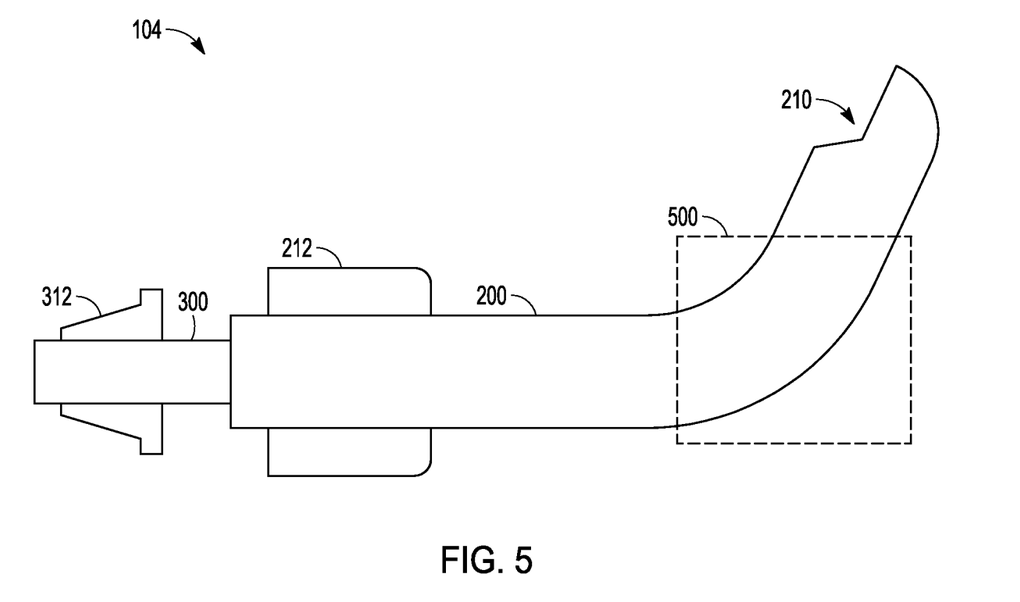
FIG. 5 shows a side view of the distal portion of the debrider of FIG. 1, as assembled, with the inner shaft positioned at least partially inside the outer shaft.

FIG. 5 shows a side view of the distal portion 104 of the debrider of FIG. 1, as assembled, with the inner shaft 300 (FIG. 3) positioned at least partially inside the outer shaft 200 (FIG. 2). When the inner shaft 300 is positioned at least partially inside the outer shaft 200, the inner shaft hub 312 can be positioned proximal to a proximal end of the outer shaft 200.

The outer shaft 200 and the inner shaft 300 can both include a bend 500. For example, the bend 500 can include a change in axial direction or longitudinal direction of the outer shaft 200 and the inner shaft 300, such that a longitudinal direction on a proximal side of the bend 500 is angled with respect to a longitudinal direction on a distal side of the bend 500. The bend 500 can include a radius of curvature. The radius of curvature can be constant over the extent of the bend 500, or can vary over the extent of the bend 500. The bend 500 can lack sharp corners, such that the longitudinal direction of the outer shaft 200 and the inner shaft 300 can change direction smoothly (e.g., without any discontinuities) along the bend 500. Such a bend 500 can allow the practitioner to access tissue with greater ease and greater precision than if the bend 500 were absent (e.g. if the outer shaft 200 and the inner shaft 300 were both straight and lacked any bends). The flexible inner shaft portion 302 (FIG. 3) of the inner shaft 300 can extend over a portion of the bend 500, over all of the bend 500, or beyond the bend 500.

In the region of the bend 500, such as including all or some of the portions of the outer shaft 200 and the inner shaft 300 over which the longitudinal directions of the outer shaft 200 and the inner shaft 300 vary in direction, the debrider can include multiple bearings between the inner shaft 300 and the outer shaft 200, along a length of the bend 500. Each bearing can optionally include multiple ball bearings that can form a single aligned ring at a single axial location along the longitudinal axis of the outer shaft 200 and the inner shaft 300. The multiple bearings can occupy different axial locations along the longitudinal axis of the outer shaft 200 and the inner shaft 300. Compared with use of a single bearing, or use of a bearing at each end of the bend 500, the multiple bearings distributed from each other at different axial locations along the length of the bend 500 can help reduce friction between the inner shaft 300 and the outer shaft 200, which can help ease a load on the actuator 106 (FIG. 1), and can help reduce wear on the inner shaft 300 and the outer shaft 200.

For a configuration in which the outer shaft 200 is rigid at the bend 500, the multiple bearings can space the flexible inner shaft portion 302 with respect to the outer shaft 200 as the inner shaft 300 moves. For a configuration in which the outer shaft 200 is flexible at the bend 500, the bearings 602 can space the flexible inner shaft portion 302 with respect to the flexible outer shaft portion 204 of the outer shaft 200 as the inner shaft 300 moves. Such spacing can help prevent or reduce contact between an outer surface of the inner shaft 300 and an inner surface of the outer shaft 200 as the inner shaft 300 moves. FIGS. 6 through 9 and the accompanying text pertain to both of these configurations.

Figure 6:
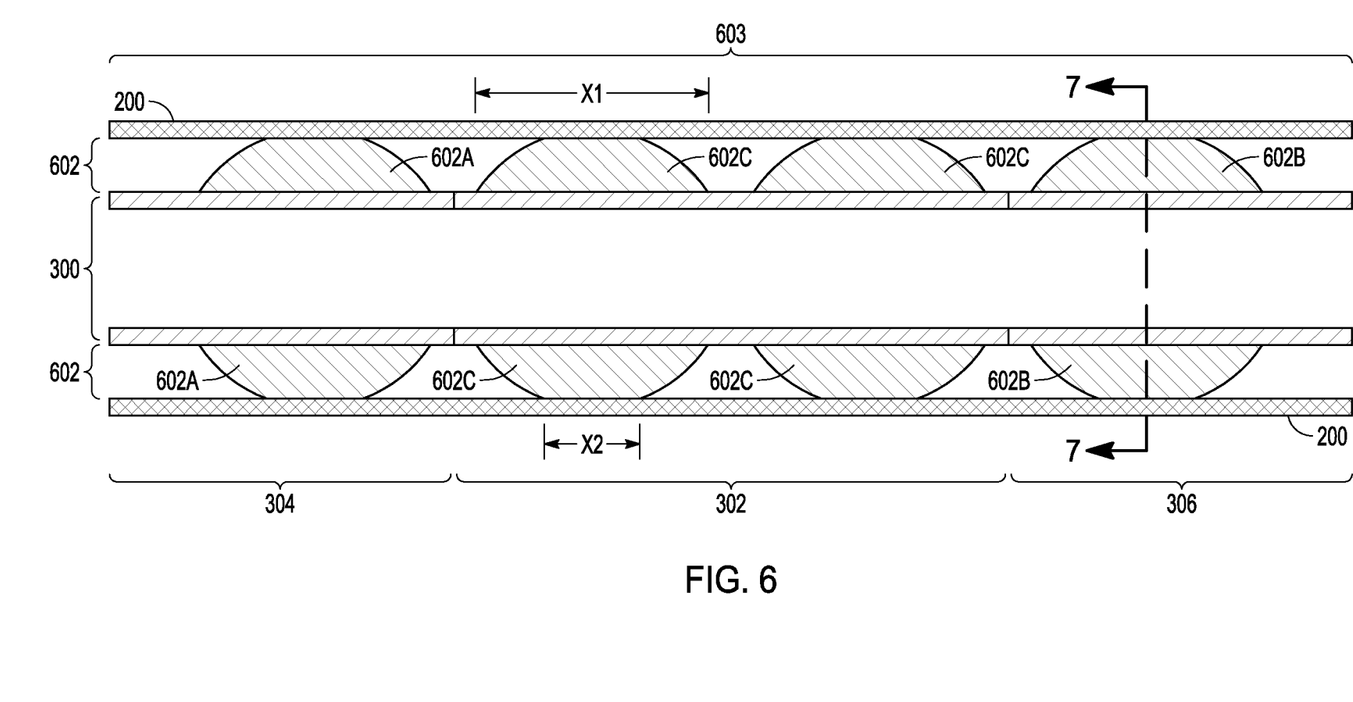
FIG. 6 shows a cross-sectional view of an example of multiple spaced-apart bearings located between the inner shaft and the outer shaft along a length of the inner shaft.

FIG. 6 shows a cross-sectional view of an example of multiple spaced-apart bearings 602 located between the inner shaft 300 and the outer shaft 200 along a length of the inner shaft 300. The bearings 602 can space the inner shaft 300 apart from the outer shaft 200 as the inner shaft 300 moves. For example, the bearings 602 can help ensure that an outer surface of the inner shaft 300 does not contact an inner surface of the outer shaft 200 as the inner shaft 300 moves during use.

For clarity, the portion of the inner shaft 300 and the outer shaft 200 is shown in FIG. 6 as being straight, rather than bent. The flexible inner shaft portion 302 can allow the inner shaft 300 to change shape in the vicinity of the bend 500. During use, the flexible inner shaft portion 302 can be bent in the vicinity of the bend 500.

The bearings 602 can be located between the inner shaft 300 and the outer shaft 200 along a length 604 of the inner shaft 300. The length 604 can include at one or more intermediate locations between end regions of the flexible inner shaft portion 302 of the inner shaft 300.

The length 604 of the inner shaft 300 can include all or part of the flexible inner shaft portion 302, which is more flexible than at least one of a more proximal portion 304 or more distal portion 306 of the inner shaft 300. For a configuration in which the outer shaft 200 is rigid, the bearings can space the flexible inner shaft portion 302 with respect to the outer shaft 200 as the inner shaft 300 moves. For a configuration in which the outer shaft 200 is flexible, the bearings can space the flexible inner shaft portion 302 with respect to the flexible outer shaft portion 204 (FIG. 2) as the inner shaft 300 moves.

The bearings 602 can be distributed to include a proximal bearing 602A located proximate a proximal portion of the flexible inner shaft portion 302. The proximal bearing 602A can be located on the flexible inner shaft portion 302, on the more proximal portion 304 (as shown in the example of FIG. 6), or can extend over both the flexible inner shaft portion 302 and the more proximal portion 304.

The bearings 602 can be distributed to include a distal bearing 602B located proximate a distal portion of the flexible inner shaft portion 302. The distal bearing 602B can be located on the flexible inner shaft portion 302 (as shown in the example of FIG. 6), on the more distal portion 306, or can extend over both the flexible inner shaft portion 302 and the more distal portion 306.

The bearings 602 can be distributed, such as to include at least one intermediate bearing 602C located between the proximal bearing 602A and the distal bearing 602B. The bearings 602 can be evenly spaced or unevenly spaced along the length 604 of the flexible inner shaft portion 302. For example, the bearings 602 can be spaced more closely together in a region of a bend that has a relatively small radius of curvature, and farther apart in a region of the bend that has a relatively large radius of curvature. The bearings 602 can optionally include a central bearing located halfway between the proximal bearing 602A and the distal bearing 602B.

At least one bearing 602 can optionally have a longitudinal extent, taken in a direction parallel to an elongation direction of the inner shaft 300 (e.g. along a horizontal direction in FIG. 6), that is greater proximate the inner shaft 300 (e.g., quantity X1) than proximate the outer shaft 200 (e.g., quantity X2). Such a difference in longitudinal extent can arise from a manufacturing process for the bearings 602, in which the bearings 602 are formed on the inner shaft 300, and the inner shaft 300 and bearings 602, together, are placed within the outer shaft 200.

The longitudinal extent can include shapes that are circular, elliptical, oval-shaped, diamond-shaped, or any other suitable shape. Two or more adjacent bearings can optionally be connected together by bearing material that extends between the adjacent bearings proximate the inner shaft 300.

Figure 7:
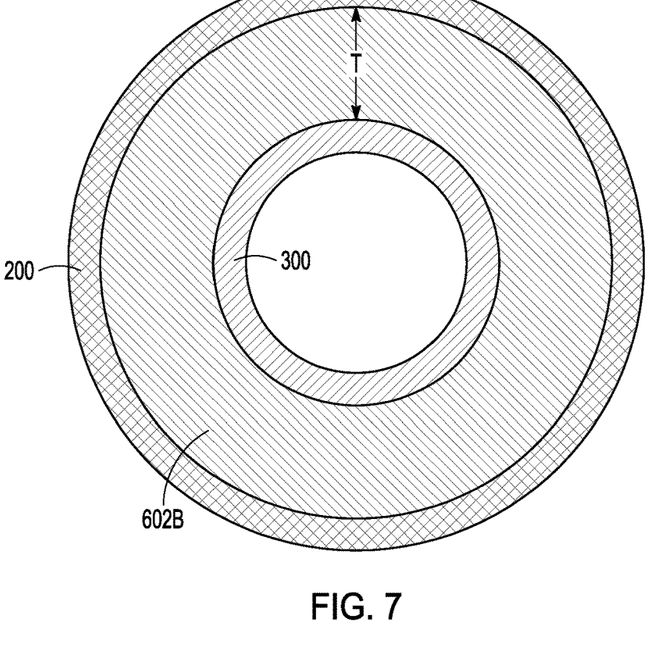
FIG. 7 shows an end-on cross-sectional view of the distal bearing of FIG. 6.

FIG. 7 shows an end-on cross-sectional view of the distal bearing 602B of FIG. 6. The distal bearing 602B can extend radially outward from an exterior of the inner shaft 300 to an interior of the outer shaft 200. The distal bearing 602B can have a distal bearing thickness (T), measured radially outward from the inner shaft 300 to the outer shaft 200. The thickness (T) can extend over a full annular space, as shown in FIG. 7, or over a portion of the annular space.

End-on cross-sections of the other bearings 602 in FIG. 6 can have similar profiles. For example, the proximal bearing 602A (FIG. 6) can have a proximal bearing thickness, measured radially outward from the inner shaft 300 to the outer shaft 200. Similarly, each intermediate bearing 602C (FIG. 6) can have a respective intermediate bearing thickness, measured radially outward from the inner shaft 300 to the outer shaft 200.

The intermediate bearing thickness (or thicknesses, for configurations that include multiple intermediate bearings 602C), the proximal bearing thickness, and the distal bearing thickness can optionally be substantially equal to one another, to within available manufacturing and alignment tolerances.

The intermediate bearing thickness (or one or more of the intermediate bearing thicknesses, for configurations that include multiple intermediate bearings 602C), can optionally be less than the proximal bearing thickness and less than the distal bearing thickness. Such differences in thickness can help compensate for deformations in any or all of the bearings 602, the inner shaft 300, or the outer shaft 200 that can occur during use. Because the deformations can vary for different locations in the bend 500 (FIG. 5), the thicknesses of the bearings 602 can also vary in a similar manner. Such differences in thickness can help compensate for wearing of one or more bearings 602 over time.

The distal bearing 602B can have an annular cross-section, taken in a plane orthogonal to an elongation direction of the inner shaft 300. The elongation direction can be parallel to a central axis of the inner shaft 300 at each longitudinal location of the inner shaft. In other words, the elongation direction can follow the inner shaft 300 around the bend 500 (FIG. 5).

Such an annular cross-section can help effectively form a seal between the inner shaft 300 and the outer shaft 200. For configurations in which the debrider can additionally include plumbing that can supply suction and/or irrigation to the cutting area, the plumbing can be located within the outer shaft 200 and outside the inner shaft 300, through one or more cut-aways in one or more of the bearings 602.

Figure 8:
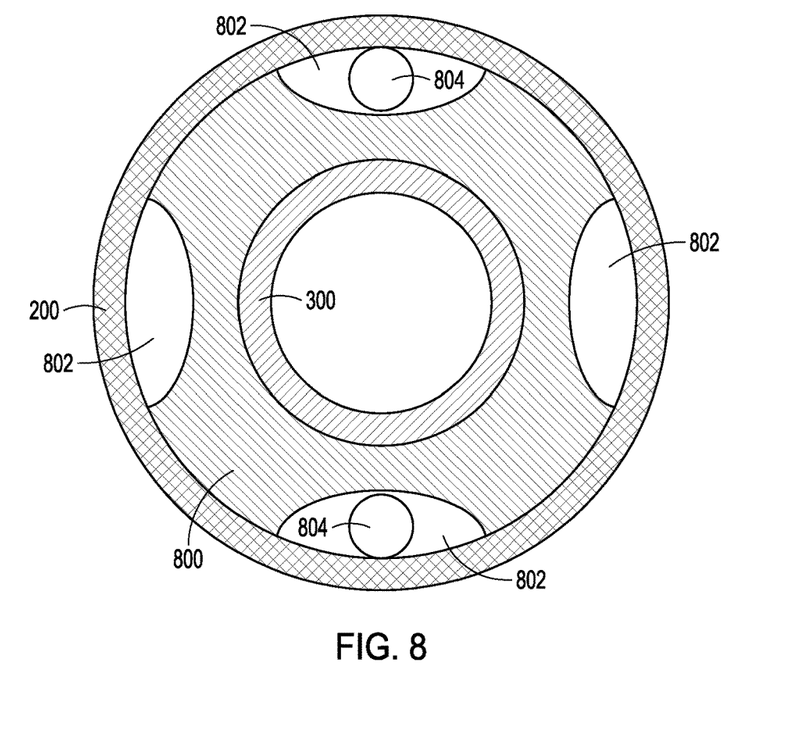
FIG. 8 shows an end-on cross-sectional view of an example of a bearing that includes one or more cut-aways at its outer periphery.

FIG. 8 shows an end-on cross-sectional view of an example of a bearing 800 that includes one or more cut-aways 802 at its outer periphery. The cut-aways 802 can accommodate plumbing for suction and/or irrigation. The plumbing can include a physical conduit in a space for passage within or attached to the outer shaft 200, a space for passage of fluids (e.g., lacking a physical conduit). The cut-aways 802 can be sized, shaped, located, arranged, or otherwise configured to accommodate corresponding electrical connections, such as to power a light source, power a camera, and/or deliver a digital signal from a camera. The cut-aways 802 can accommodate corresponding pull wires, such as which can controllably position and reposition the distal portion of the debrider, if needed.

One or more tubes 804 can extend along the outer shaft 200, inside the outer shaft 200 and outside the inner shaft 300, through a cut-away 802 of each bearing 800. One tube 804 can provide suction to a distal portion of the debrider. One tube can 804 provide irrigation to a distal portion of the debrider. As an alternative to using the tubes 804, the tubes 804 may be omitted, and the suction and/or the irrigation can be provided directly through one or more of the cut-aways 802 without the tubes 804.

Figure 9:
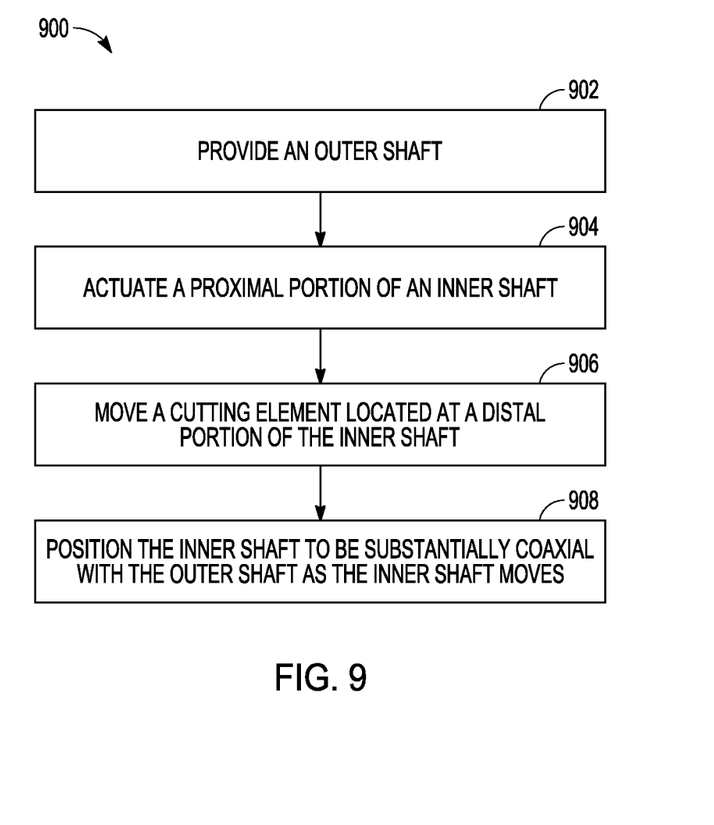
FIG. 9 shows a flow chart for an example of a method for operating a debrider.

FIG. 9 shows a flow chart for an example of a method 900 for operating a debrider. The method 900 can be executed by the debrider 100 of FIG. 1, or by any suitable debrider. The method 900 is but one method for operating a debrider; other suitable methods can also be used.

At operation 902, the debrider can provide an elongated, hollow outer shaft. The outer shaft can include a flexible outer shaft portion that is more flexible than at least one of a more proximal or more distal portion of the outer shaft.

At operation 904, the debrider can actuate a proximal portion of an elongated inner shaft that is at least partially disposed within the outer shaft to impart movement to the inner shaft. The inner shaft can include a flexible inner shaft portion that is more flexible than at least one of a more proximal or more distal portion of the inner shaft. At least some of the flexible inner shaft portion can be disposed within the flexible outer shaft portion.

At operation 906, the debrider can move, via the inner shaft, a cutting element located at a distal portion of the inner shaft. The outer shaft can expose the cutting element as the inner shaft moves.

At operation 908, the debrider can position, via a plurality of bearings located between the inner shaft and the outer shaft along a length of the inner shaft, the flexible inner shaft portion to be substantially coaxial with the flexible outer shaft portion as the inner shaft moves.

The structures, techniques, and methods described thus far have been in the context of a debrider, in which an actuator or motor can apply motion to a proximal end of an inner shaft to affect motion of a cutting element located at a distal end of the inner shaft. Similar structures, techniques, and methods can also be applied to a drill. For example, an actuator or motor can apply a rotation to a proximal end of an inner shaft to rotate a drill bit located at a distal end of the inner shaft. The drill can include multiple bearings located between the inner shaft and an outer shaft along a length of the inner shaft. The length of the inner shaft can include one or more intermediate locations between end regions of a flexible inner shaft portion. The bearings can space the flexible inner shaft portion with respect to the outer shaft as the inner shaft moves. The multiple bearings can be used for other suitable applications in which an inner shaft can move with respect to an outer shaft.

EXAMPLES

To further illustrate the surgical device and/or method discussed herein, a non-limiting list of examples is provided below. Each of the following non-limiting examples can stand on its own, or can be combined in any permutation or combination with any one or more of the other examples.

In Example 1, a surgical device can include: an elongated, hollow outer shaft; an elongated inner shaft movable within the outer shaft and including a flexible inner shaft portion that is more flexible than at least one of a more proximal or more distal portion of the inner shaft; a cutting element located at a distal portion of the inner shaft and configured to move with the inner shaft, the outer shaft configured to expose the cutting element as the inner shaft moves; and a plurality of bearings located between the inner shaft and the outer shaft along a length of the inner shaft, the bearings configured to space the flexible inner shaft portion with respect to the outer shaft as the inner shaft moves.

In Example 2, the surgical device of Example 1 can optionally be configured such that the plurality of bearings is located between the inner shaft and the outer shaft along the length including at one or more intermediate locations between end regions of the flexible inner shaft portion.

In Example 3, the surgical device of any one of Examples 1-2 can optionally be configured such that the movement of the inner shaft within the outer shaft comprises at least one of single-direction rotation about a central axis, oscillating rotation about the central axis, or reciprocating translation along the central axis.

In Example 4, the surgical device of any one of Examples 1-3 can optionally be configured such that the plurality of bearings includes: a proximal bearing located proximate a proximal portion of the flexible inner shaft portion, a distal bearing located proximate a distal portion of the flexible inner shaft portion, and at least one intermediate bearing located between the proximal bearing and the distal bearing.

In Example 5, the surgical device of any one of Examples 1-4 can optionally be configured such that: the proximal bearing has a proximal bearing thickness, measured radially outward from the inner shaft to the outer shaft; the distal bearing has a distal bearing thickness, measured radially outward from the inner shaft to the outer shaft; a first intermediate bearing, of the at least one intermediate bearing, has an intermediate bearing thickness, measured radially outward from the inner shaft to the outer shaft; and the intermediate bearing thickness is less than the proximal bearing thickness and less than the distal bearing thickness.

In Example 6, the surgical device of any one of Examples 1-5 can optionally be configured such that: the proximal bearing has a proximal bearing thickness, measured radially outward from the inner shaft to the outer shaft; the distal bearing has a distal bearing thickness, measured radially outward from the inner shaft to the outer shaft; a first intermediate bearing, of the at least one intermediate bearing, has an intermediate bearing thickness, measured radially outward from the inner shaft to the outer shaft; and the intermediate bearing thickness, the proximal bearing thickness, and the distal bearing thickness are substantially equal to one another.

In Example 7, the surgical device of any one of Examples 1-6 can optionally be configured such that the plurality of bearings are evenly spaced along the length of the flexible inner shaft portion.

In Example 8, the surgical device of any one of Examples 1-7 can optionally be configured such that the plurality of bearings are unevenly spaced along the length of the flexible inner shaft portion.

In Example 9, the surgical device of any one of Examples 1-8 can optionally be configured such that at least one bearing, of the plurality of bearings, has an annular cross-section, taken in a plane orthogonal to an elongation direction of the inner shaft.

In Example 10, the surgical device of any one of Examples 1-9 can optionally be configured such that at least one bearing, of the plurality of bearings, has a generally annular cross-section, taken in a plane orthogonal to an elongation direction of the inner shaft, with at least one cut-away at its outer periphery.

In Example 11, the surgical device of any one of Examples 1-10 can optionally be configured such that each bearing, of the plurality of bearings, has a generally annular cross-section, taken in a plane orthogonal to an elongation direction of the inner shaft, with at least one cut-away at its outer periphery.

In Example 12, the surgical device of any one of Examples 1-11 can optionally further include a tube extending along the outer shaft, inside the outer shaft and outside the inner shaft, through a cut-away of each bearing.

In Example 13, the surgical device of any one of Examples 1-12 can optionally be configured such that at least one bearing, of the plurality of bearings, has a longitudinal extent, taken in a direction parallel to an elongation direction of the inner shaft, that is greater proximate the inner shaft than proximate the outer shaft.

In Example 14, the surgical device of any one of Examples 1-13 can optionally further include an actuator configured to controllably impart movement to a proximal portion of the inner shaft, the inner shaft being configured to transmit the imparted movement along the inner shaft to move the cutting element, the imparted movement being at least one of single-direction rotation about a central axis, oscillating rotation about the central axis, or reciprocating translation along the central axis.

In Example 15, the surgical device of any one of Examples 1-14 can optionally be configured such that the cutting element comprises at least one of a shaving blade or a burr.

In Example 16, a method for operating a surgical device can include: providing an elongated, hollow outer shaft; actuating a proximal portion of an elongated inner shaft that is at least partially disposed within the outer shaft to impart movement to the inner shaft, the inner shaft including a flexible inner shaft portion that is more flexible than at least one of a more proximal or more distal portion of the inner shaft; moving, via the inner shaft, a cutting element located at a distal portion of the inner shaft, the outer shaft configured to expose the cutting element as the inner shaft moves; and positioning, via a plurality of bearings located between the inner shaft and the outer shaft along a length of the inner shaft, the flexible inner shaft portion to be substantially coaxial with the outer shaft as the inner shaft moves.

In Example 17, the method of Example 16 can optionally be configured such that the plurality of bearings includes: a proximal bearing located proximate a proximal portion of the flexible inner shaft portion, a distal bearing located proximate a distal portion of the flexible inner shaft portion, and at least one intermediate bearing located between the proximal bearing and the distal bearing.

In Example 18, the method of any one of Examples 16-17 can optionally be configured such that: the proximal bearing has a proximal bearing thickness, measured radially outward from the inner shaft to the outer shaft; the distal bearing has a distal bearing thickness, measured radially outward from the inner shaft to the outer shaft; a first intermediate bearing, of the at least one intermediate bearing, has an intermediate bearing thickness, measured radially outward from the inner shaft to the outer shaft; and the intermediate bearing thickness is less than the proximal bearing thickness and less than the distal bearing thickness.

In Example 19, the method of any one of Examples 16-18 can optionally be configured such that: the proximal bearing has a proximal bearing thickness, measured radially outward from the inner shaft to the outer shaft; the distal bearing has a distal bearing thickness, measured radially outward from the inner shaft to the outer shaft; a first intermediate bearing, of the at least one intermediate bearing, has an intermediate bearing thickness, measured radially outward from the inner shaft to the outer shaft; and the intermediate bearing thickness, the proximal bearing thickness, and the distal bearing thickness are substantially equal to one another.

In Example 20, a surgical device can include: an elongated, hollow outer shaft; an elongated inner shaft movable within the outer shaft and including a flexible inner shaft portion that is more flexible than at least one of a more proximal or more distal portion of the inner shaft; an actuator configured to controllably impart movement to a proximal portion of the inner shaft, the inner shaft being configured to transmit the imparted movement along the inner shaft to a distal portion of the inner shaft, the imparted movement being at least one of single-direction rotation about a central axis, oscillating rotation about the central axis, or reciprocating translation along the central axis; a cutting element located at the distal portion of the inner shaft and configured to move with the inner shaft, the outer shaft configured to expose the cutting element as the inner shaft moves; and a plurality of bearings located between the inner shaft and the outer shaft along the flexible inner shaft portion, the bearings configured to space the flexible inner shaft portion with respect to the outer shaft as the inner shaft moves.

What is claimed is:

1. A surgical device, comprising:
   an elongated, hollow outer shaft;
   an elongated inner shaft movable within the outer shaft and including a flexible inner shaft portion that is more flexible than at least one of a more proximal or more distal portion of the inner shaft;
   a cutting element located at a distal portion of the inner shaft and configured to move with the inner shaft, the outer shaft configured to expose the cutting element as the inner shaft moves; and a plurality of bearings located between the inner shaft and the outer shaft along a length of the inner shaft, the bearings configured to space the flexible inner shaft portion with respect to the outer shaft as the inner shaft moves, the plurality of bearings including a proximal bearing located proximate a proximal portion of the flexible inner shaft portion, the proximal bearing having a proximal bearing thickness measured radially outward from the inner shaft to the outer shaft, the plurality of bearings including a distal bearing located proximate a distal portion of the flexible inner shaft portion, the distal bearing having a distal bearing thickness measured radially outward from the inner shaft to the outer shaft, the plurality of bearings including an intermediate bearing located between the proximal bearing and the distal bearing, the intermediate bearing having an intermediate bearing thickness measured radially outward from the inner shaft to the outer shaft, the intermediate bearing thickness being less than the proximal bearing thickness and less than the distal bearing thickness.

2. The surgical device of claim 1, wherein the plurality of bearings is located between the inner shaft and the outer shaft along the length including at one or more intermediate locations between end regions of the flexible inner shaft portion.

3. The surgical device of claim 1, wherein the movement of the inner shaft within the outer shaft comprises at least one of single-direction rotation about a central axis, oscillating rotation about the central axis, or reciprocating translation along the central axis.

4. The surgical device of claim 1, wherein the plurality of bearings are evenly spaced along the length of the flexible inner shaft portion.

5. The surgical device of claim 1, wherein the plurality of bearings are unevenly spaced along the length of the flexible inner shaft portion.

6. The surgical device of claim 1, wherein at least one bearing, of the plurality of bearings, has an annular cross-section, taken in a plane orthogonal to an elongation direction of the inner shaft.

7. The surgical device of claim 1, wherein at least one bearing, of the plurality of bearings, has a generally annular cross-section, taken in a plane orthogonal to an elongation direction of the inner shaft, with at least one cut-away at its outer periphery.

8. The surgical device of claim 1, wherein each bearing, of the plurality of bearings, has a generally annular cross-section, taken in a plane orthogonal to an elongation direction of the inner shaft, with at least one cut-away at its outer periphery.

9. The surgical device of claim 8, further comprising a tube extending along the outer shaft, inside the outer shaft and outside the inner shaft, through a cut-away of each bearing.

10. The surgical device of claim 1, wherein at least one bearing, of the plurality of bearings, has a longitudinal extent, taken in a direction parallel to an elongation direction of the inner shaft, that is greater proximate the inner shaft than proximate the outer shaft.

11. The surgical device of claim 1, further comprising an actuator configured to controllably impart movement to a proximal portion of the inner shaft, the inner shaft being configured to transmit the imparted movement along the inner shaft to move the cutting element, the imparted movement being at least one of single-direction rotation about a central axis, oscillating rotation about the central axis, or reciprocating translation along the central axis.

12. The surgical device of claim 1, wherein the cutting element comprises at least one of a shaving blade or a burr.

13. A method for operating a surgical device, the method comprising:

providing an elongated, hollow outer shaft;

actuating a proximal portion of an elongated inner shaft that is at least partially disposed within the outer shaft to impart movement to the inner shaft, the inner shaft including a flexible inner shaft portion that is more flexible than at least one of a more proximal or more distal portion of the inner shaft;

moving, via the inner shaft, a cutting element located at a distal portion of the inner shaft, the outer shaft configured to expose the cutting element as the inner shaft moves; and positioning, via a plurality of bearings located between the inner shaft and the outer shaft along a length of the inner shaft, the flexible inner shaft portion to be substantially coaxial with the outer shaft as the inner shaft moves, the plurality of bearings including a proximal bearing located proximate a proximal portion of the flexible inner shaft portion, the proximal bearing having a proximal bearing thickness measured radially outward from the inner shaft to the outer shaft, the plurality of bearings including a distal bearing located proximate a distal portion of the flexible inner shaft portion, the distal bearing having a distal bearing thickness measured radially outward from the inner shaft to the outer shaft, the plurality of bearings including an intermediate bearing located between the proximal bearing and the distal bearing, the intermediate bearing having an intermediate bearing thickness measured radially outward from the inner shaft to the outer shaft, the intermediate bearing thickness being less than the proximal bearing thickness and less than the distal bearing thickness.

14. A surgical device, comprising:

an elongated, hollow outer shaft;

an elongated inner shaft movable within the outer shaft and including a flexible inner shaft portion that is more flexible than at least one of a more proximal or more distal portion of the inner shaft;

an actuator configured to controllably impart movement to a proximal portion of the inner shaft, the inner shaft being configured to transmit the imparted movement along the inner shaft to a distal portion of the inner shaft, the imparted movement being at least one of single-direction rotation about a central axis, oscillating rotation about the central axis, or reciprocating translation along the central axis;

a cutting element located at the distal portion of the inner shaft and configured to move with the inner shaft, the outer shaft configured to expose the cutting element as the inner shaft moves; and a plurality of bearings located between the inner shaft and the outer shaft along the flexible inner shaft portion, the bearings configured to space the flexible inner shaft portion with respect to the outer shaft as the inner shaft moves, the plurality of bearings including a proximal bearing located proximate a proximal portion of the flexible inner shaft portion, the proximal bearing having a proximal bearing thickness measured radially outward from the inner shaft to the outer shaft, the plurality of bearings including a distal bearing located proximate a distal portion of the flexible inner shaft portion, the distal bearing having a distal bearing thickness measured radially outward from the inner shaft to the outer shaft, the plurality of bearings including an intermediate bearing located between the proximal bearing and the distal bearing, the intermediate bearing having an intermediate bearing thickness measured radially outward from the inner shaft to the outer shaft, the intermediate bearing thickness being less than the proximal bearing thickness and less than the distal bearing thickness.

15. The surgical device of claim 14, wherein the plurality of bearings are evenly spaced along the length of the flexible inner shaft portion.

16. The surgical device of claim 14, wherein the plurality of bearings are unevenly spaced along the length of the flexible inner shaft portion.

17. The surgical device of claim 14, wherein at least one bearing, of the plurality of bearings, has an annular cross-section, taken in a plane orthogonal to an elongation direction of the inner shaft.

18. The surgical device of claim 14, wherein at least one bearing, of the plurality of bearings, has a generally annular cross-section, taken in a plane orthogonal to an elongation direction of the inner shaft, with at least one cut-away at its outer periphery.

19. The surgical device of claim 14, wherein:
each bearing, of the plurality of bearings, has a generally annular cross-section, taken in a plane orthogonal to an elongation direction of the inner shaft, with at least one cut-away at its outer periphery; and
the surgical device further comprises a tube extending along the outer shaft, inside the outer shaft and outside the inner shaft, through a cut-away of each bearing.

20. The surgical device of claim 14, wherein at least one bearing, of the plurality of bearings, has a longitudinal extent, taken in a direction parallel to an elongation direction of the inner shaft, that is greater proximate the inner shaft than proximate the outer shaft.

* * * * *